United States Patent
Steiner et al.

(10) Patent No.: US 11,576,596 B2
(45) Date of Patent: Feb. 14, 2023

(54) HAND-HELD APPLICATOR

(71) Applicant: BÜHLMANN LABORATORIES AG, Schönenbuch (CH)

(72) Inventors: Lukas Steiner, Buchs AG (CH); Cédric Wernli, Allschwil (CH); Gregor Naef, Niederrohrdorf (CH); Daniel Gygax, Himmelried (CH); Jakob Weber, Pfeffingen (CH)

(73) Assignee: BÜHLMANN LABORATORIES AG, Schönenbuch (CH)

(*) Notice: Subject to any disclaimer, the term of this patent is extended or adjusted under 35 U.S.C. 154(b) by 916 days.

(21) Appl. No.: 16/469,240

(22) PCT Filed: Dec. 14, 2017

(86) PCT No.: PCT/EP2017/082831
§ 371 (c)(1),
(2) Date: Jun. 13, 2019

(87) PCT Pub. No.: WO2018/109091
PCT Pub. Date: Jun. 21, 2018

(65) Prior Publication Data
US 2020/0029878 A1    Jan. 30, 2020

(30) Foreign Application Priority Data
Dec. 15, 2016 (EP) .................................... 16204501

(51) Int. Cl.
*A61B 5/15* (2006.01)
*B01L 3/02* (2006.01)

(52) U.S. Cl.
CPC .. *A61B 5/150755* (2013.01); *A61B 5/150099* (2013.01); *A61B 5/150236* (2013.01);
(Continued)

(58) Field of Classification Search
CPC ........ A61B 5/150755; A61B 5/150099; A61B 5/150236; A61B 5/150351;
(Continued)

(56) References Cited

U.S. PATENT DOCUMENTS 8,372,353 B2  2/2013  Lee
8,723,964 B2  5/2014  Wakefield
(Continued)

FOREIGN PATENT DOCUMENTS

EP    2676608      12/2013
JP    H01-276842   11/1989
(Continued)

OTHER PUBLICATIONS

International Search Report for PCT/EP2017/082831 dated Jan. 23, 2018.

*Primary Examiner* — Dennis White
(74) *Attorney, Agent, or Firm* — Hueschen and Sage

(57) ABSTRACT

A hand-held applicator (10) for collecting, mixing, diluting and discharging a sample liquid, comprising a main body (20) having an inlet-aperture (24), an outlet-aperture (26) and a chamber (22) for storing a liquid solution, wherein the chamber is connected to the inlet-aperture and the outlet-aperture, a lid (12) for covering the inlet-aperture and a tube (40), moveably supported in the inlet-aperture when the lid is covering the upper portion of the main body, wherein the tube (40) is moveable between a predetermined position outside the chamber and a position, in which the tube is at least partly located in the chamber.

17 Claims, 3 Drawing Sheets

(52) U.S. Cl.
CPC ........ *A61B 5/150351* (2013.01); *B01L 3/021* (2013.01); *B01L 2300/042* (2013.01); *B01L 2300/044* (2013.01); *B01L 2300/0838* (2013.01); *B01L 2400/0406* (2013.01)

(58) Field of Classification Search
CPC ........ A61B 5/150343; A61B 5/150259; A61B 5/150022; B01L 3/021; B01L 2300/042; B01L 2300/044; B01L 2300/0838; B01L 2400/0406; B01L 3/502; B01L 3/0272; B01L 2300/0825; B01L 2400/0478; B01L 3/5027; B01L 2200/027; B01L 2300/0672
See application file for complete search history.

(56) References Cited

U.S. PATENT DOCUMENTS

| | | |
|---|---|---|
| 2005/0196872 A1 | 9/2005 | Nguyen |
| 2008/0081378 A1 | 4/2008 | Ramel |
| 2012/0101407 A1 | 4/2012 | Chan |
| 2013/0216452 A1* | 8/2013 | Phan ...................... B01L 3/508 422/547 |
| 2015/0182156 A1* | 7/2015 | Engbersen ....... G01N 33/54366 435/7.94 |

FOREIGN PATENT DOCUMENTS

| | | |
|---|---|---|
| JP | 2007-585541 | 3/2007 |
| JP | 2007-527537 | 9/2007 |
| JP | 2009-543895 | 12/2009 |
| JP | 2010-536815 | 11/2010 |
| JP | 2015-523894 | 8/2015 |
| WO | WO2008/008187 | 1/2008 |
| WO | WO2013/025899 | 2/2013 |
| WO | WO2015160552 | 10/2015 |

\* cited by examiner

HAND-HELD APPLICATOR

FIELD OF THE INVENTION

The invention relates to a hand-held applicator for collecting, mixing, diluting and discharging a liquid solution, in particular blood.

PRIOR ART

Presently, it is complicated to test at the point of care a small amount of solution like whole blood. The blood has to be taken from a patient and often needs to be mixed with a solution that is usually prepared in a small test tube. The solution mixed with the blood is then taken out from the test tube by a pipette and put onto a test stripe or a microchannel which can be provided in a test device for testing substances contained in the mixed solution.

DISCLOSURE OF INVENTION

Object of the present invention is to provide an apparatus which can easily handle the collecting, mixing, diluting and discharging of a liquid solution sample.

This object is solved by an apparatus according to present claim 1. Preferred embodiments of the invention are depicted in the dependent claims.

An inventive hand-held applicator for collecting, mixing, diluting and discharging a sample liquid comprises a main body having an inlet-aperture, an outlet-aperture and a chamber for storing a liquid solution, wherein the chamber is connected to the inlet-aperture and the outlet-aperture, a lid for covering the inlet-aperture and a tube, moveably supported in the inlet-aperture when the lid is covering the upper portion of the main body, wherein the tube is moveable between a predetermined position outside the chamber and a position, in which the tube is at least partly located in the chamber. Such a hand-held applicator is an easy way for a non-laboratory-professional user or a patient to take a patient's or his own blood and mix it with a solution for further application onto a test device.

The chamber comprises an inlet opening for introducing the sample taken with the tube into the chamber, the inlet opening is preferably covered by a breakable closure or a seal. In this way, the liquid can be provided and kept in the apparatus, but can easily be mixed with a collected sample by breaking the seal with a tube. Furthermore, the chamber also has an outlet opening through which the solution and mixture, respectively, in the chamber can flow out. The outlet opening can preferably also be sealed by a breakable seal to ensure that the liquid solution is kept in the chamber until the seal is broken. Preferably, the plunger comprises a channel for discharging the solution contained in the chamber.

Preferably, the outlet opening is provided on a protrusion on the bottom of the chamber or on top of a moveable plunger. Particularly, the protrusion protrudes into the chamber by a predetermined height. By this, the amount or volume of liquid discharged through the outlet opening of the chamber can be predetermined, by simultaneously ensuring that a small amount or volume of the mixed solution is left in the applicator.

Furthermore, the hand-held applicator can comprise a plunger supporting the tube, wherein the plunger is movably accommodated in the inlet-aperture. In such an embodiment the tube is arranged in the main body and does not have to be put back into a channel in the main body after use, which makes use of the tube safer and easier.

Furthermore, the lid comprises preferably a protrusion (in particular in axial direction) and the main body has a first and second abutment surface, the second abutment surface is located lower than and rotationally offset from the first abutment surface. In this way, this ensures that the lid has two positions, one before use of the hand-held applicator, and one that enables mixing of the taken liquid sample.

The lid of the hand held applicator comprises a protrusion in axial direction and the main body has a stopper for defining a first position for the lid. That ensures that the breakable closure or seal cannot be damaged by accident.

Furthermore, the apparatus might also comprise a breakable closure that covers the connection of the chamber to the outlet aperture. By this it is avoided that accidently some of the mixed sample can be discharged, since at first the breakable closure has to be opened.

Furthermore, a plunger can be moveably supported by the outlet aperture, wherein the plunger comprises a channel for discharging the solution contained in the chamber. This plunger is a means for breaking the breakable closure at the outlet aperture.

The tube for taking the blood works preferably by means of a capillary force. I.e. the tube has a diameter small enough to suck up the liquid to be tested without any additional means.

In one embodiment, the chamber in a closed state or the capsule in a closed state is subject to low pressure to enhance the flow of the uptaken liquid sample out of the tube into the mixing chamber.

Preferably, the breakable seal is a thin foil, for example made of plastics, or a membrane.

The outlet-aperture can be covered by a second lid to avoid accidental activation of the second outlet.

The inlet-aperture on the top of the main body comprises preferably a tapered portion. That eases the introduction of the tube of the uptaken liquid sample. However, this is only beneficial if the tube is fixed in the lid. In another embodiment, the tube is fixed in the inlet aperture so that it is not necessary to introduce the tube into the inlet aperture again after taking the sample.

Preferably, the outlet-aperture comprises a thread for enabling the hand-held applicator being screwed on a test device. This enables a fixed connection of the hand-held applicator on the test device while discharging the mixed solution. In another embodiment, the outlet aperture is configured to be plugged onto a protrusion of the test device.

A method according to the invention for collecting, mixing, diluting and discharging a sample liquid by means of an held-held applicator, wherein the hand-held applicator has a main body, a lid and a tube, comprising the steps removing the lid from the main body, collecting the sample liquid by means of the tube, covering the main body with the lid, pushing the lid thereby driving the tube into a chamber of the main body which stores a liquid solution, mixing the sample with the liquid solution and placing the hand-held applicator on a test device.

BRIEF DESCRIPTION OF THE FIGURES

FIG. 1 shows a longitudinal section of the first embodiment of the present invention in an isometric view;

FIG. 2 shows a schematic sequence of steps for using the apparatus of FIG. 1;

PREFERRED EMBODIMENTS

Figures 1, 2:
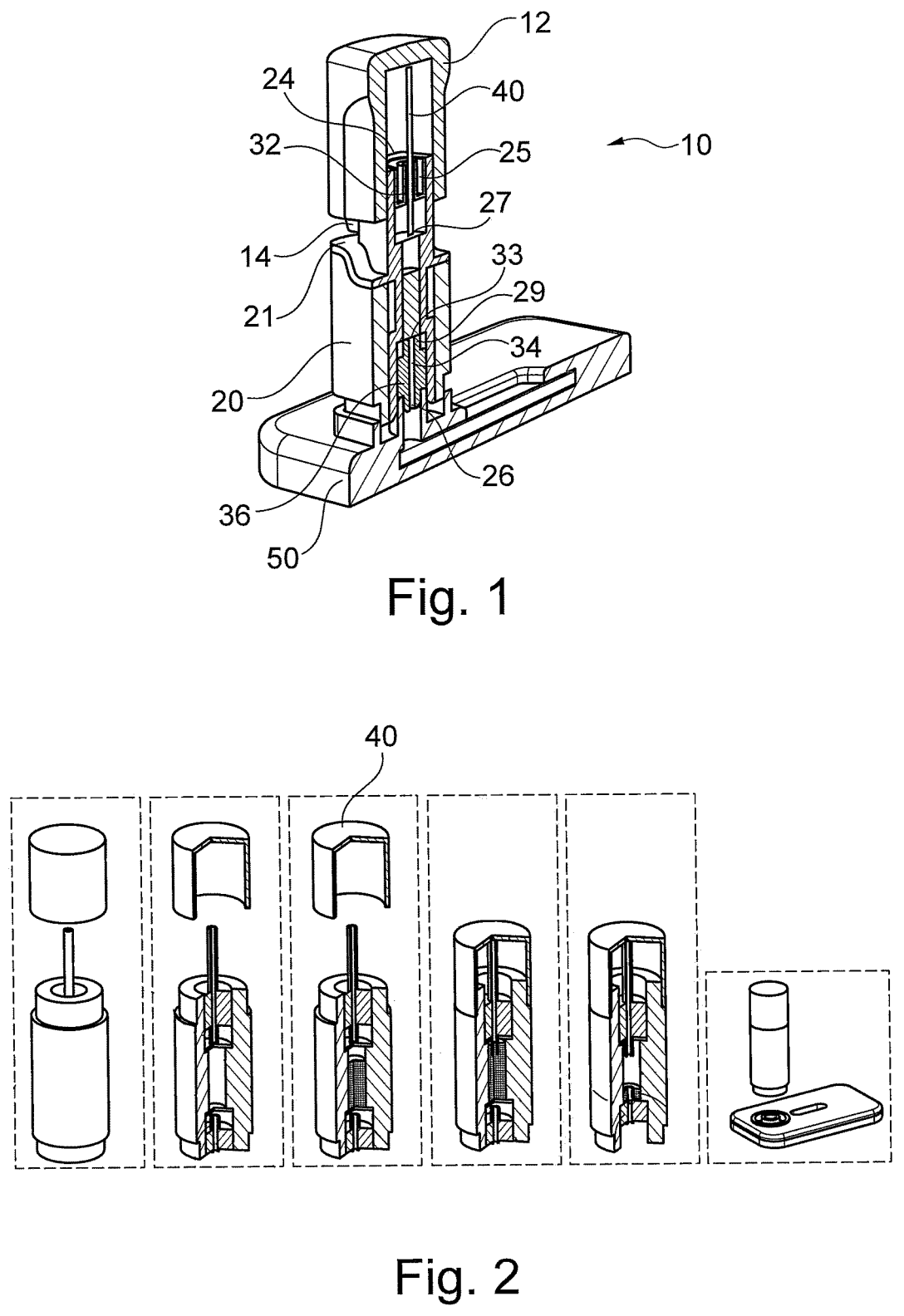
Figure 3:
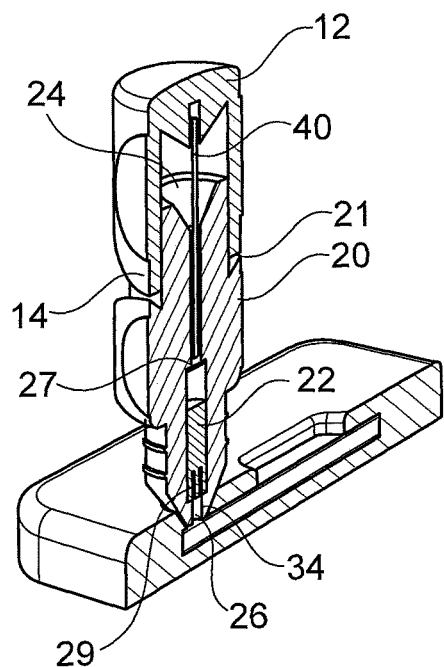
FIG. 3 shows a longitudinal section of a second embodiment of the present invention in an isometric view.

In the following, directions are referred to as they are shown in the FIGS. 1-4. I.e. the inlet aperture is on the upper part of the apparatus, while the outlet aperture is on the lower part of the apparatus. Furthermore, the directions "axial" (in a longitudinal direction of the apparatus), "radial" (rectangular to the longitudinal direction) and "circumferential" (around the longitudinal direction) are used with regard to the longitudinal axis of the apparatus.

A hand-held applicator 10 comprises a main body 20 with a chamber 22. The chamber is formed into the main body, preferably in the center of the main body. The chamber is filled with a solution that is to be mixed with a sample liquid collected with a tube as described below. In the following, the solution mixed with the sample liquid will be called "mixed solution" or "mixture". The main body 20 has an inlet aperture 24 for accommodating and supporting a tube 30 or for introducing a tube 30 for collecting a liquid sample and an outlet aperture 26 for discharging a solution or mixture contained in the chamber 22.

The inlet aperture 24 is formed in the main body and leads to an inlet opening 27 of the chamber 22 via a channel 32 formed in the main body 20. The inlet aperture 24 is preferably inclined on the top surface of the main body. I.e. the inlet has a tapered or conical shape like a funnel. Generally, the upper channel 32 only needs to be big enough to accommodate a tube 40 for collecting a liquid sample, but it can also be configured to match the size of the tube 40 to guide the tube to the chamber or to support it if the tube is mounted and held in the main body. The main body can comprise additional elements, for example an additional guidance or supporting element 25 for the tube 40, wherein the element 25 is arranged at the upper part of the main body and preferably comprises the inlet aperture. The inlet aperture 24 can be tapered at the inside on the top, so as to ease insertion of the tube 40. As shown in FIG. 3, the tapered portion can be formed over the whole width of the main body. However, the tapered portion may also comprise just the adjacent area around the inlet aperture 24, e.g. in an area with a diameter of about 1-5 mm.

The outlet opening 29 is formed on the bottom of the chamber 22 and is connected via a lower channel 34 with the outlet aperture 26 of the main body 20. The outlet opening 29 serves to enable the solution to flow out of the chamber when the hand-held applicator 10 is placed on a test device that is configured to analyze or test the mixed solution. This outlet opening 26 is preferably provided on top of a protrusion, so that not the entire mixture flows out when the outlet aperture 26 is opened or activated and connected to the outlet opening 29 of the main body, but a defined amount of mixture remains on the bottom of the chamber below the outlet on the protrusion. The inner part of the protrusion can comprise a breakable seal as described below. Another embodiment of the protrusion can be formed as a small tube that is configured to keep the liquid in the chamber by a capillary force. In this embodiment, the inner part of the tube does preferably not comprise a seal, since the solution will only flow out of the chamber when the capillary force is released by putting the hand-held apparatus on the test device. In another embodiment of the chamber, the bottom of the chamber can be formed of a breakable seal. In such an embodiment, the outlet opening 29 comprises a plunger 36 as described below.

The outlet opening 29 of the chamber 22 and/or the outlet aperture 26 of the main body 20 can be formed in a plunger 36 that is moveably supported on the lower portion of the main body 20. This plunger 36 is able to glide in an axial direction and serves to move to the outlet opening of the chamber and is in particular configured to activate the discharge of the solution present in the chamber. The plunger 36 is accommodated in a bigger channel at the bottom of the main body 20 and is preferably provided with a protrusion on the upper side and/or on the lower side. The upper protrusion can serve to break the seal, if one is present at the bottom of the chamber 22, and it can also provide the outlet opening for the chamber 22 and/or the outlet opening 29 of the main body 20. When the protrusion is pushed into the chamber 22, it will preferably protrude above the bottom of the chamber 22 so as to avoid that all the solution will flow out of the chamber as described above. The plunger 36 can comprise a small circumferential groove for a seal like a rubber ring that serves to tightly seal the contact between the main body 20 and the plunger 36.

In one embodiment, the chamber 22 is preferably configured to hold a solution that is to be mixed with the liquid introduced by the tube 40 to generate the mixed solution. As described above, the upper end of the chamber 22 is sealed with a breakable seal so as to keep the solution within the chamber 22. The breakable seal can be a foil or a membrane and is stable enough to keep the solution in the chamber 22, but soft or weak enough so that the seal can be penetrated by the tube 40. Depending on the material, the breakable seal has a thickness of 0.1 to 1 mm. The outlet opening 26 can also be sealed with the same kind of breakable seal as described above for the inlet opening. In one embodiment, the top and/or the bottom of the chamber can completely be made of the breakable seal.

A second lid can be provided at the lower part of the main body 10. Such a lid can accommodate the lower portion and can serve to close the outlet opening to prevent accidental discharge of the solution or the mixed solution In another embodiment, the chamber is configured to accommodate a capsule including the solution. Such a capsule also comprises a seal at the upper and lower end, also for the purpose for keeping the solution inside the capsule. The rest of the capsule is configured as the above described chamber. Such a capsule is easily exchangeable and could enable the hand-held apparatus to be used repeatedly. On both, the sealed chamber and the capsule can be applied a low pressure. This low pressure serves to ease the sample liquid held in the tube to be discharged into the chamber for mixing the sample liquid with the solution.

Figure 4:
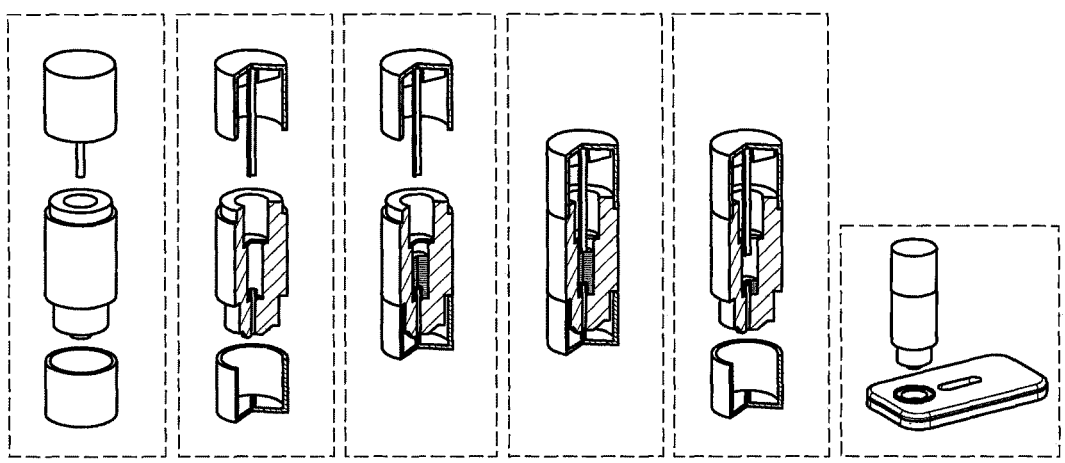
FIG. 4 shows a schematic sequence of steps for using the apparatus of FIG. 3.

The inlet aperture 24 is covered by a detachable lid 12. The lid 12 has a closed end and an open end which is to be placed on the hand-held apparatus 10. The lid 12 has a shape that matches the main body of the hand-held apparatus. Preferably, the main body 20 and the lid 12 have a square, rectangular, oval or circular cross section. Preferably, the lid 12 comprises on the open end one or more protrusions 14 in axial direction. On the main body 20 is provided a stopper 21 which serves to stop the lid 12 from being pushed further into the main body 20 than a predetermined first position. To apply the liquid in the tube to the chamber 22, the lid 12 is rotated so that the protrusion 14 does not abut against the stopper 21 and the lid 12 can be pushed further inwards into the main body 20 until it reaches a completely closed position. The rotation can be done by means of a thread and will preferably comprise merely a rotation of about 90° degree as shown in FIGS. 2 and 4. The lid is in the first position at the start of the thread, and after a rotation of 90° it is in the second position. The second position is used after the liquid sample has been taken and the tube is pushed into the chamber.

In case the lid supports the tube as shown in FIG. 3, the lid can comprise a device for generating a low pressure at the end of the tube to provide the tip of the end with a suction force. The suction force can for example be generated with a balloon on the inside of the lid that is connected with one end of the tube 40 and pressed together and released when the tip of the tube 40 comes into contact with the liquid sample. For this, the lid can have windows in on the side so as to enable the fingers of the user to press the balloon. The actuation of the balloon can also be carried out automatically when the user presses a button provided on the lid that activates an automated small pump arranged in the lid.

The tube 40 is preferably formed as a thin tubing of an outer diameter of about 0.5 to 2 mm with a small through hole (inner diameter, respectively) of 0.3 to 1 mm. The tip of the tube 40 serves to collect a sample liquid like for example blood. This is preferably done by a capillary force while touching the sample liquid with the tip of the tube 40. Furthermore, it is also possible to collect the liquid sample by sucking it in the tube 40 with help of a low pressure applied to the tip. The low pressure can be applied by pressing a rubber ball filled with air that is formed at the holding end of the tube 40 and generates a suction at the tip like a pipette. The tip of the tube 40 directed to the chamber 22 in the closed state of the hand-held apparatus 10 can in particular be cut off in an angle so that a sharpened tip is formed to ease perforating the breakable seal. In another embodiment, the end of the tube 40 has a circumferential bezel for the same purpose of sharpening the tip. However, the diameter of the tube 40 is big enough to avoid a danger for the patient when collecting a sample liquid.

In one embodiment shown in FIG. 1, the tube 40 is arranged in the main body 20, where it is supported and moveably fixed in the inlet aperture 24 as to enable the movement of the tube 40 to be pushed into the chamber. For that purpose, the tube can also be fixed in a moveable plunger arranged in the inlet aperture 24. This is an easy way to fixedly and stably secure the tube, but ensure the movability of the tube in the main body 20. In another embodiment shown in FIG. 3, the tube 40 is fixedly arranged in the lid 12, in particular in the center on the bottom at the closed end of the lid 12.

Figure 5:
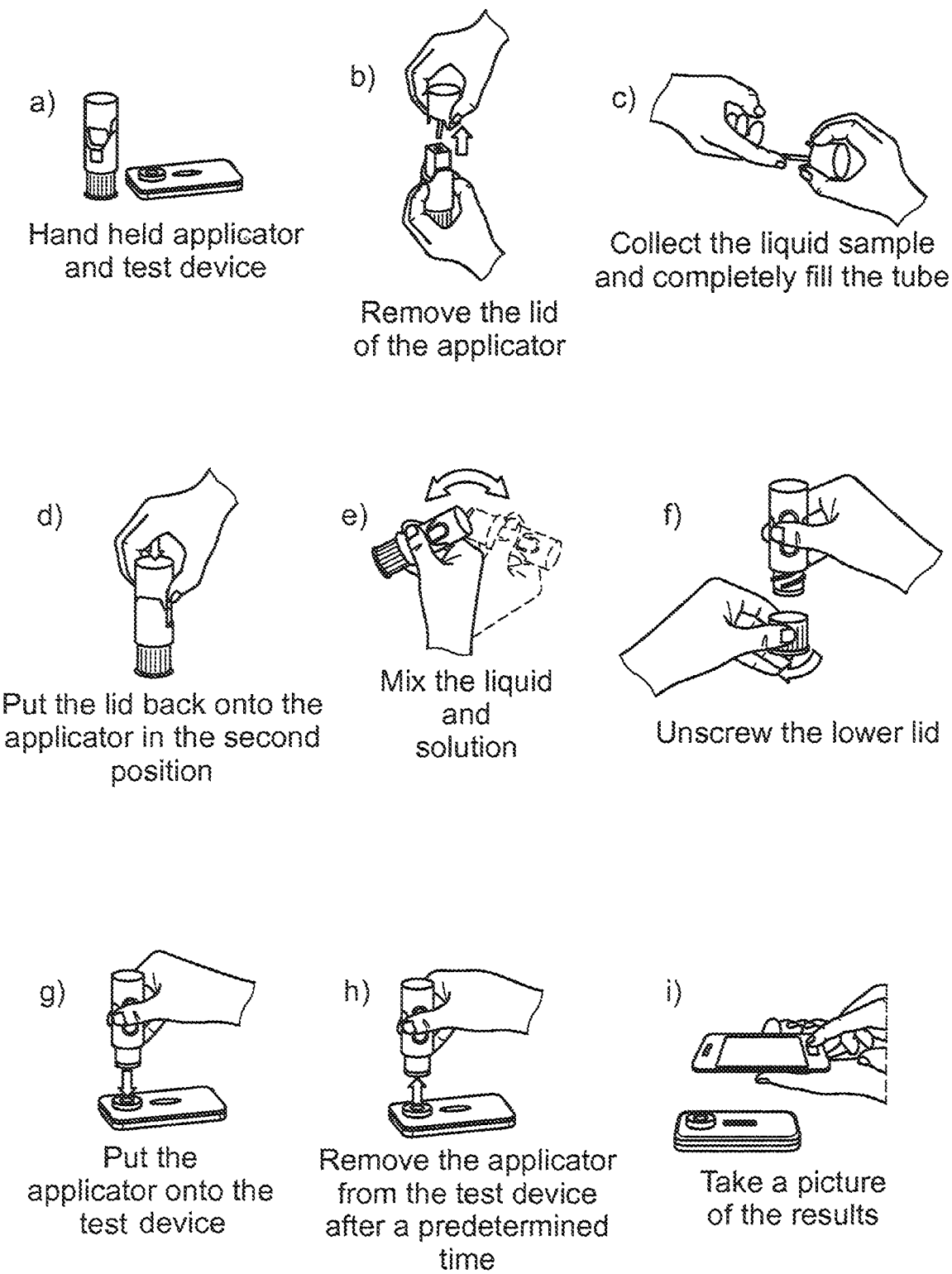
FIG. 5 a-i shows a sequence of method steps according to the invention.

The use of the hand-held apparatus 10 for collecting a sample liquid is described in the following (see also FIGS. 5 a to i). After unpacking the hand-held apparatus 10, the lid 12 is arranged on top of the main body 20 in the first position so that the tube 40 is not protruding into the chamber 22 (FIG. 5a). The lid 12 is taken off the main body 20 (FIG. 5b) and depending whether the tube 40 is supported by the main body or the lid 12, the respective element is guided to the sample and the tip of the tube 40 is brought into contact with the liquid sample. By a capillary force or with other means mentioned above, the liquid is sucked into the hollow portion inside the tube 40 (FIG. 5c). If the tube 40 is supported and held by the lid 12, the tube is then introduced into the inlet opening 27, and if the tube 40 is supported by the main body 20, the lid 12 is placed on top of the main body 20, encompassing the tube 40 as well. The lid 12 is rotated such that a possible protrusion is not abutting against the stopper 21. After that, the lid 12 is pushed down such that the tube 40 is pushed through the breakable seal into the chamber 22 or capsule and is brought in contact with the solution within the chamber 22 or capsule (FIG. 5d). If there is a breakable seal, the tube is pushed through the seal and breaks it. By that contact with the solution within the chamber 22, the sample liquid within the hollow portion of the tube 40 is flowing into the chamber 22 and can be mixed with the solution. Thereby, the lid 12 is tightly fixed on the top of the main body to prohibit discharge of the mixed solution out of the inlet opening 27 and inlet aperture 24. For mixing the solution properly with the sample liquid, the hand-held apparatus 10 can be manually shaken (FIG. 5e) or also be placed in a special shaking device. After mixing the sample liquid with the solution in the chamber 22 to acquire a mixed solution, the lower lid is unscrewed from the hand-held device 10 if there is a lid (FIG. 5f) and/or it is placed on the loading port 51 of a test device 50 (FIG. 5g). The loading port 51 is configured to activate the outlet aperture 26 and the outlet opening 29. In the present embodiment of FIG. 1, this is done by a plunger 36 that is pushed upwards against and trough a breakable seal 34, thereby opening the outlet aperture 26. Other possibilities comprise a protrusion on the test device that is pushed into the outlet opening 29 and the outlet aperture 26. In yet another embodiment, the outlet aperture 26 might be provided with a thread or a thread-like pattern into which a protrusion of the test device can be screwed or accordingly placed onto. By screwing or accordingly placing the hand-held applicator onto the test device, the protrusion of the test device can puncture the bottom of the chamber 22 and start the discharge of the mixed solution. When the outlet is opened, the mixture of the solution and the sample liquid flows onto the test device 50 and a test stripe or microchannel will then carry out analyzing or testing the mixture and showing the result as it is known to the skilled person or a respectively trained patient. In an embodiment in which the mixture is kept in the chamber by means of a capillary force, the test device will release this capillary force and the mixture flows onto the test device 50 as described above. In case a protrusion is formed on the bottom in the chamber or that the plunger has a protrusion that protrudes into the chamber above the bottom, a predetermined amount of mixed solution will be left in the chamber. This amount of mixed solution may serve as a means to re-check the results, if necessary. Finally, the hand-held applicator 10 is removed from the test device 50 (FIG. 5h) and the test results can be shown on a display for further use, e.g. taking a picture (FIG. 5i).

LIST OF REFERENCE NUMBERS hand-held applicator 10
lid 12
protrusions 14
main body 20
stopper 21
chamber 22
inlet aperture 24
supporting element 25
outlet aperture 26
inlet opening 27
outlet opening 29
tube 30
upper channel 32
lower channel 34
plunger 36 tube 40
test device 50
loading port 51

The invention claimed is:

1. A hand-held applicator (10) for collecting, mixing, diluting and discharging a sample liquid, comprising
   a main body (20) having an inlet-aperture (24), an outlet-aperture (26) and a chamber (22) for storing a liquid solution, wherein the chamber (22) is connected to the inlet-aperture (24) and the outlet-aperture (26);
   a lid (12) for covering the inlet-aperture (24); and
   a tube (40), moveably supported in the inlet-aperture (24) when the lid (12) is covering the upper portion of the main body (20), wherein the tube (40) is moveable between a predetermined position outside the chamber (22) and a position, in which the tube (40) is at least partly located in the chamber (22), wherein,
   an outlet-opening (29) of the chamber (22) is provided on a protrusion on the bottom of the chamber (22) or on a protrusion on top of a moveable plunder (36) that is accommodated in a bottom portion of the main body (20).

2. The hand-held applicator according to claim 1, wherein the tube (40) is supported by a plunger that is movably accommodated in the inlet-aperture (24).

3. The hand-held applicator according to claim 1, wherein the chamber (22) consists of a breakable capsule.

4. The hand-held applicator according to claim 1, wherein the lid (12) comprises a protrusion in axial direction and the main body has a stopper for defining a first position for the lid (12).

5. The hand-held applicator according to claim 4, wherein the lid may be rotated about 90° degrees to be moved into a second position.

6. The hand-held applicator according to claim 1, wherein the tube (40) is connected with the lid (12).

7. The hand-held applicator according to claim 1, wherein the chamber (22) comprises at least one breakable seal to cover the inlet opening (27) and/or the outlet opening (29) of the chamber.

8. The hand-held applicator according to claim 1, wherein the plunger comprises a channel for discharging the solution contained in the chamber (22) or the capsule.

9. The hand-held applicator according to claim 1, wherein the tube (40) is filled with a sample liquid by means of capillary force.

10. The hand-held applicator according to claim 1, wherein the tube (40) is mounted in the lid (12) and the lid (12) comprises means to provide a suction force on the tip of the tube (40).

11. The hand-held applicator according to claim 1, wherein low-pressure is applied to the chamber (22) in a closed state.

12. The hand-held applicator according to claim 7, wherein the at least one breakable seal is a foil or membrane.

13. The hand-held applicator according to claim 1, wherein the outlet-aperture (26) is covered by a second lid.

14. The hand-held applicator according to claim 1, wherein the inlet-aperture (24) comprises a tapered portion.

15. The hand-held applicator according to claim 1, wherein the outlet-aperture (26) comprises a thread for enabling the hand-held applicator being screwed on a test device.

16. A Method for collecting, mixing, diluting and discharging a sample liquid by means of a hand-held applicator of claim 1, comprising the steps
    removing the lid (12) from the main body (20);
    collecting the sample liquid by means of the tube (40);
    covering the main body (20) with the lid (12);
    pushing the lid (12) thereby driving the tube (40) into a chamber (22) of the main body (20) which stores a liquid solution;
    mixing the sample with the liquid solution;
    placing the hand-held applicator on a test device (50); and
    releasing the mixed sample and liquid solution onto a loading port (51) of the test device (50).

17. The method according to claim 16, wherein the step of releasing the sample mixture comprises pushing or screwing the hand-held applicator (10) onto the loading port (51) of the test device (50).

\* \* \* \* \*

UNITED STATES PATENT AND TRADEMARK OFFICE
CERTIFICATE OF CORRECTION

PATENT NO. : 11,576,596 B2
APPLICATION NO. : 16/469240
DATED : February 14, 2023
INVENTOR(S) : Lukas Steiner et al.

Page 1 of 1

It is certified that error appears in the above-identified patent and that said Letters Patent is hereby corrected as shown below:

On the Title Page

Page 2, Column 2, "FOREIGN PATENT DOCUMENTS":
The fourth reference should read -- 2010-536,015 --.

Signed and Sealed this
Fourth Day of April, 2023

Katherine Kelly Vidal
*Director of the United States Patent and Trademark Office*